United States Patent [19]

Crenner

[11] Patent Number: 5,626,575

[45] Date of Patent: May 6, 1997

[54] POWER LEVEL CONTROL APPARATUS FOR ELECTROSURGICAL GENERATORS

[75] Inventor: James C. Crenner, Golden, Colo.

[73] Assignee: Conmed Corporation, Utica, N.Y.

[21] Appl. No.: 431,013

[22] Filed: Apr. 28, 1995

[51] Int. Cl.⁶ ............................................. A61B 17/39
[52] U.S. Cl. ........................ 606/34; 606/39; 606/40; 606/42
[58] Field of Search ............................... 606/34–52

[56] References Cited

U.S. PATENT DOCUMENTS

| | | |
|---|---|---|
| 3,801,800 | 4/1974 | Newton . |
| 4,378,801 | 4/1983 | Oosten ........................ 606/37 |
| 4,545,375 | 10/1985 | Cline . |
| 4,590,934 | 5/1986 | Malis et al. . |
| 4,632,109 | 12/1986 | Paterson . |
| 4,827,927 | 5/1989 | Newton . |
| 5,160,334 | 11/1992 | Billings et al. . |
| 5,217,457 | 6/1993 | Delahuerga et al. . |
| 5,226,904 | 7/1993 | Gentelia et al. . |
| 5,234,427 | 8/1993 | Ohtomo et al. . |
| 5,244,462 | 9/1993 | Delahuerga et al. . |

Primary Examiner—David M. Shay
Attorney, Agent, or Firm—Larson and Taylor

[57] ABSTRACT

An electrosurgical generator system includes an electrosurgical handpiece including an active electrode for receiving electrosurgical power from a generator, and cut and coagulation mode switches and a foot activated switch device also including cut and coagulation mode switches. A signal processor associated with the generator and connected to the handpiece and foot activated switch device monitors the states of the cut and coagulation mode switches so as to detect activation of any of these switches and, responsive to two successive activations of a single switch of the switches being monitored, provides control of the power produced by the electrosurgical generator by further activation of the single switch.

22 Claims, 4 Drawing Sheets

POWER LEVEL CONTROL APPARATUS FOR ELECTROSURGICAL GENERATORS

BACKGROUND OF THE INVENTION

1. Field of the Invention

The present invention relates to electrosurgical generators and, more particularly, to an improved electrosurgical generator system which enables the power output of the electrosurgical generator of the system to be remotely adjusted by the operator.

2. The Prior Art

A common electrosurgical generator unit provides for adjusting or changing the power output of the generator by the surgeon or other operator using controls at the main controller, i.e., at the control keypad or control panel of the generator, and for controlling at least two different high frequency current outputs for the purpose of cutting or coagulation using switches on the handpiece with which surgery is performed. In this system, the main controller of the unit is outside of the sterile field and is also used to set the particular mode (cutting or coagulation) while the handpiece switches simply activate or interrupt the high frequency current outputs. In other systems, mode selection but not power adjustment can be made at the handpiece. In either event, the need to adjust the power output at the main controller is a disadvantage in that while the surgeon can provide off-on control and, in some units, can control the mode by actuating cut or coagulation switches at the handpiece in the sterile field, the surgeon cannot adjust power in the sterile field and must rely on an assistant to do this.

One approach to the problem is to provide additional switches at the handpiece to enable changing of both the output mode and the power setting from the sterile field. An example of this approach is discussed in U.S. Pat. No. 4,632,109 to Paterson and 4,827,927 to Newton. While this approach enables the level of power delivered by the generator to be changed without having to return to the control panel of the generator (which, as stated, is outside the sterile field), the approach suffers several important disadvantages, including a lack of interchangeability with more conventional units and problems with design due to considerations of controllability and limited installation space.

A further approach to this problem is disclosed in U.S. Pat. No. 5,234,427 to Ohtomo et al. In this patent the handpiece includes cutting and coagulation mode switches and the operator can perform a mode change (e.g., from normal coagulation to spray coagulation) within the sterile field by depression of these two switches simultaneously. In some embodiments, the two switches are simultaneously closed to provide a mode change and a "set-input means" is used to enable the surgeon to cycle through, in a predetermined order, a plurality of different modes. When a particular mode is selected, a "set-process means" instructs the system to change a particular "operating condition" associated with that mode such as the output power of the coagulation mode. In this example, the cutting mode switch can then be used as a level increasing key for increasing the coagulation output power and the coagulation mode switch can be used as a level decreasing switch for decreasing the coagulation output power. Although the electrosurgical unit disclosed in the Ohtomo et al. patent decreases the number of keys that must be provided on the handpiece, the unit suffers disadvantages with respect to the switch manipulations necessary (including, in particular, the need for simultaneous actuation of the coagulation and cutting switches) and the relative complexity of "set-input means" and of the interplay between this "means" and the switch manipulations.

SUMMARY OF THE INVENTION

In accordance with the invention, an electrosurgical generator system is provided which permits the surgeon in the sterile field to use a single hand and/or foot activated switch to enter a mode of operation, referred to as the remote power adjust mode, wherein the power can be adjusted using the hand or foot switch, in addition to the normal adjustment at the front panel of the generator.

Preferably, the power adjustment provided by the selected switch enables adjustment of coagulation power up or down and, in an advantageous embodiment, the coagulation power is adjusted down from the existing setting. Similarly, in a further preferred implementation, the power adjustment provided by the selected switch enables adjustment of the cut power up or down and, in an advantageous embodiment, the cut power is adjusted up from the existing setting.

According to a further important feature, the single hand/or foot activated switch permits the surgeon to return the system to the normal mode of operation and, in a preferred embodiment, to enter or leave the power adjustment mode through plural activations of a single hand or foot activation switch within a predetermined time period.

According to a preferred embodiment thereof, the invention comprises an electrosurgical generator system including an electrosurgical generator for producing electrosurgical power; an electrosurgical handpiece including an active electrode for receiving electrosurgical power from the generator, a first coagulation mode switch for, when activated, providing a coagulation mode of operation of the generator, and a first cut mode switch for, when activated, providing a cut mode of operation of the generator; and a foot activated switch device including a second coagulation mode switch for, when activated, providing the coagulation mode of operation of the generator and a second cut mode switch for, when activated, providing the cut mode of operation of the generator; the generator further including signal processing means connected to the handpiece and the foot activated switch device for monitoring the state of at least one of the first and second coagulation mode switches and the first and second cut mode switches so as to detect any activation of the at least one switch being monitored, and for, responsive to at least two successive activations of a single switch of the at least one switch being monitored, providing control of the power produced by the electrosurgical generator by further activation of the single switch.

Preferably, the signal processing means monitors the states of all of the switches, i.e., the cut and coagulation mode switches of both the handpiece and the foot activated device.

In an implementation wherein the electrosurgical generator includes a plurality of incremental power settings ranging between a maximum setting and a minimum setting, the signal processing means determines whether the single switch is a coagulation mode switch or a cut mode switch and provides for, responsive to the single switch being a cut mode switch, incrementing the existing power setting if that setting is less than the maximum setting and for, responsive to the single switch being a coagulation mode switch, decrementing the existing power setting if that setting is greater than the minimum setting.

Advantageously, the system further comprises tone generator means, controlled by the signal processing means, for generating a second tone during the remote power adjust mode when the single switch is a cut mode switch and for generating a third tone when during the remote power adjust mode when the single switch is a coagulation mode switch.

In a preferred embodiment, the processing means executes a test sequence prior to entering the remote power adjust mode wherein activation of the coagulation mode switches and cut mode switches are monitored, the signal processing means canceling the test sequence when activation of an activation switch does not meet a predetermined requirement. Preferably, the test sequence is canceled based on requirements concerning the activation duration and the time between activations of the switch being monitored.

Other features and advantages of the invention will be set forth in, or apparent from, the following detailed description of preferred embodiments of the invention.

DESCRIPTION OF THE PREFERRED EMBODIMENTS

Figure 1:
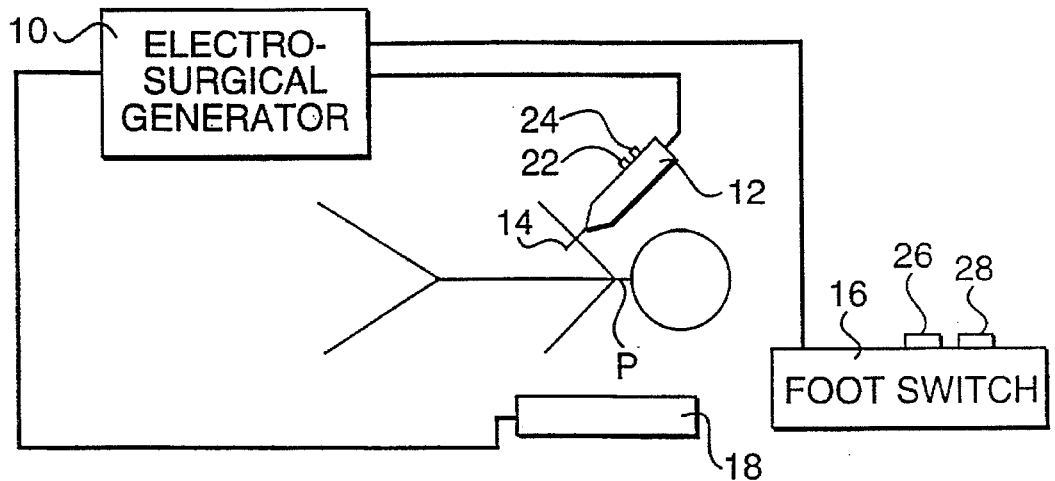
FIG. 1 is a schematic representation, partially in block diagram form, of a conventional electrosurgical generator system including a handpiece and a foot switch controller or device.

Referring to FIG. 1, there is shown a schematic representation of a generalized electrosurgical generator system. The system includes an electrosurgical generator 10 connected to an electrosurgical handpiece or "pencil" 12 with an active electrode 14, an electrosurgical foot switch controller 16 and a dispersive electrode or ground return pad 18 which is applied to the patient.

Figure 2:
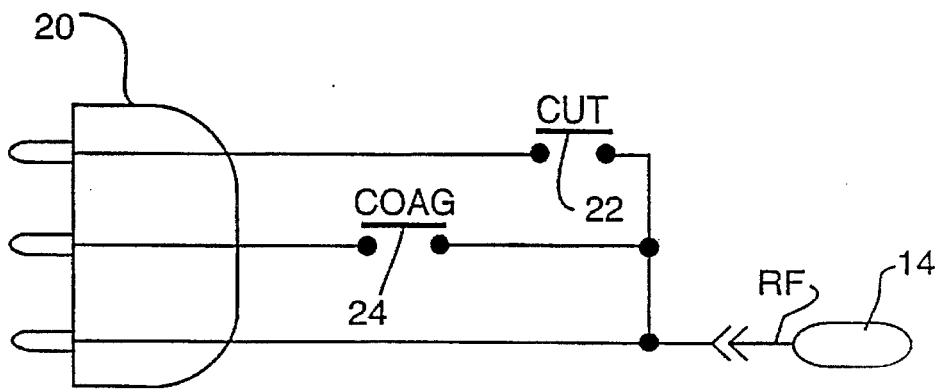
FIG. 2 is a schematic circuit diagram of electrical circuitry associated with the handpiece of FIG. 1.

A schematic circuit diagram of the electrosurgical circuitry of the handpiece 12 is shown in FIG. 2 and includes a three-connector plug 20, and a "cut" switch 22 and "coag" switch 24 connected in parallel and connected to respective connectors of plug 20. Electrode 14 is connected through the radio frequency (RF) line to the three connector prongs of plug 20. Switches 22 and 24 respectively control operation of the system in the "cut" mode (which is, generally speaking, used in cutting of tissue) and the coagulation or "coag" mode (which, generally speaking, is used in promoting coagulation of the blood, i.e., hemostasis). It will, of course, be appreciated that such handpieces are quite conventional and may include other activation or control switches.

Figure 3:
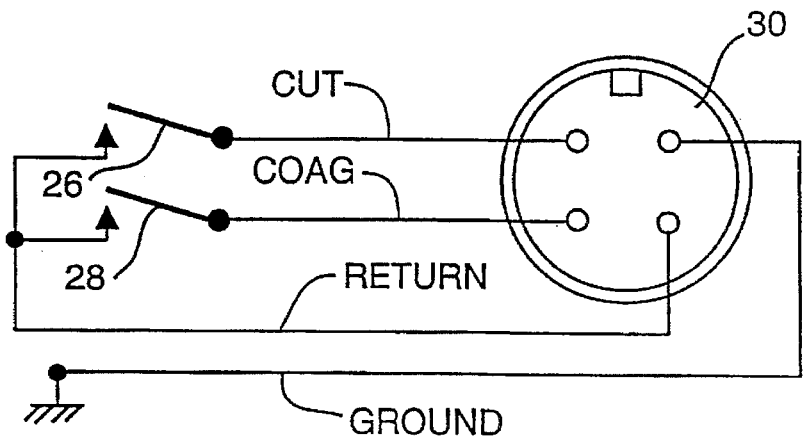
FIG. 3 is a schematic circuit diagram of electrical circuitry associated with the foot switch controller of FIG. 1.

The electrical circuitry associated with foot switch controller 16 is shown in FIG. 3 and similarly includes a "cut" switch 26 and a "coag" switch 28 connected to two terminals to a four-terminal plug 30. Return and ground lines are connected to the other two terminals. Again, the construction and operation of such a foot switch controller are conventional.

In the normal operating mode of the system of FIG. 1, activation of the electrode 14 of the handpiece 12, provided by pressing one of the various activating switches 22, 24, 26 and 28, will result in the generation of "cut" or "coag" electrosurgical current depending on which switch is depressed. As discussed above, the present invention provides a remote power adjustment mode, produced in response to double activation of any one of the activation switches 22, 24, 26 and 28, wherein a power adjustment can be selected or canceled.

Figure 4:
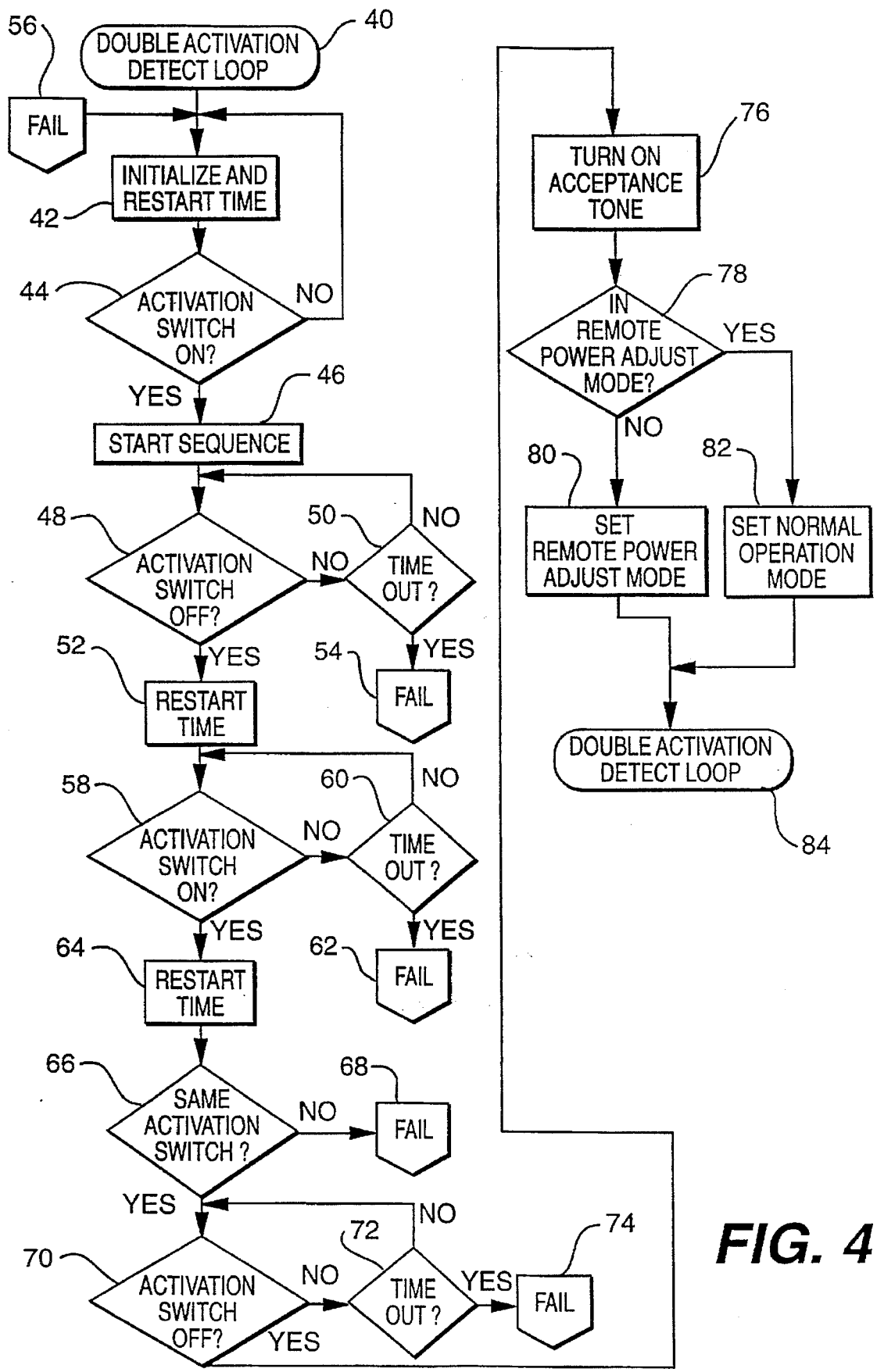
FIG. 4 is a flow chart of a double activation detect loop in accordance with a preferred embodiment of the invention.

Referring to FIG. 4, a flow chart is shown of the double activation detect loop including a start block 40 from which the sequence proceeds to an "initialize and restart time" operation, as indicated by block 42. After this operation is completed, a determination is made as whether one of the activation switches 22, 24, 26 and 28 has been activated, as is indicated by decision diamond 44 which branches back to the beginning of the sequence for a "no" and on to a "start sequence" block 46 for a "yes." Thus, if the sequence has not been triggered, then initialization is performed again and the delay start time is restarted.

After the sequence is started, the "activation" switch, i.e., the switch whose activation triggered the start, is checked to determine whether the switch is off, as is indicated by decision diamond 48 which branches to a further "time out" decision diamond 50 and to a further "restart time" block 52. Thus, if the activation switch is not released before a predetermined period (typically less then 200 milliseconds) has elapsed, as indicated by "time out?" decision diamond, the sequence fails as indicated by "fail" indicator 54 and the sequence is canceled and begins again as indicated by the "fail" indicator 56 at the beginning of the sequence. If the timer has not timed out, the test at decision diamond 48 is repeated.

If the activation switch is off, i.e., released in time, the sequence continues as indicated by "restart time" block 52 and the switch is checked again at decision diamond 58 before a predetermined time period elapses (again typically less then 200 milliseconds). If this time elapses before the switch is pressed, as indicated by a further "time out?" decision diamond 60, the sequence fails, as indicated by "fail" indicator 62, and the entire sequence is canceled to begin again at the beginning as before.

If the activation switch is pressed in a timely manner so that diamond 58 branches to "restart time" block 64, the sequence continues and the "present" activation switch, i.e., the switch currently on, is compared with the last activation switch as indicated by decision diamond 66. If the answer is "no," the sequence branches to fail, as indicated by "fail" indicator 68, whereas if the switches are the same (i.e., the answer is "yes"), the activation switch is again checked to see if it has been released, i.e., if it is "off."

As indicated by decision diamond 70, if the activation switch has not been released (i.e., if the answer is "no") and the timer has timed out (typically less than 200 milliseconds) as determined by the "time out?" decision diamond 72, the sequence fails as indicated by "fail" indicator 74 is canceled again If the answer is "yes", indicating that the activation switch has been released in time, the double activation sequence has been successful. In this instance, an acceptance tone is generated as indicated by operation block 76 and/or another indication is produced (e.g., by lighting of an indicator bulb).

When the sequence is successful, a determination is made as to whether the remote power adjust mode has been entered, as represented by decision diamond 76, and if "no," the remote power adjust mode is set. The latter is discussed below in connection with FIG. 5. If the answer is "yes," the normal operation mode is set as indicated by operational block 82. Thus, it will be appreciated that the double activation of the same switch provides a way to return to the normal operating mode from the remote power adjust mode if the system is already in the latter mode. In either event, the loop is now completed, as indicated at block 84, and returns to start.

Figure 5:
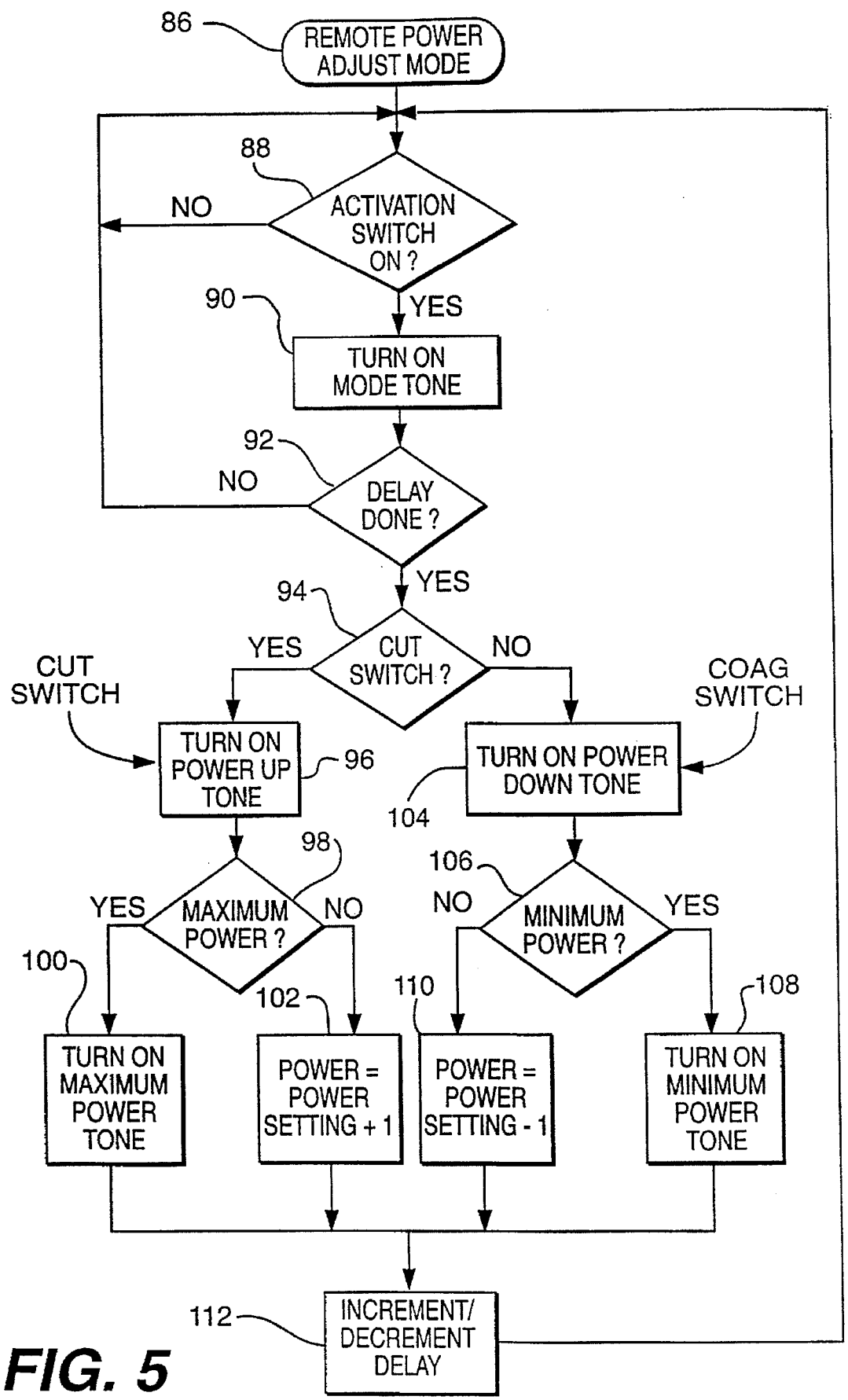
FIG. 5 is a flow chart of a remote power adjust mode sequence in accordance with a preferred embodiment of the invention.

Referring now to FIG. 5, the start of the remote power adjust mode is indicated at 86 and, as shown, the sequence first checks or determines whether the activation switch is still on as indicated by decision diamond 88. If "yes," the mode tone is turned on as represented by block 90. Thus, activation of the activation switch in the power adjust mode will turn on the mode tone and, in addition, will initialize a delay. As the sequence proceeds, a check is made whether a preset delay period has elapsed, as indicated by decision diamond 92. This delay is set to be longer than the predetermined time period for the first activation to allow determination of the results of the double activation sequence. If the switch is pressed for an elapsed time greater than the delay period, i.e., if the answer to "delay done?" is yes, then the power setting may be modified.

At this stage, a determination is then made as to which type of switch, cut or coag, was activated and to this end, a "cut-switch?" decision diamond 94 is provided. If the answer is "yes," a "power up" tone is generated as indicated by operation block 96 and a determination is made as to whether the system is at maximum power, as indicated by "maximum power?" decision diamond 98. If the answer is "yes," a "maximum power" tone is generated as indicated by operational block 100 while if the answer is "no," the power setting is incremented by 1 as indicated by operational block 102. Thus, as long as the original power setting in the cut mode is less than maximum (so that the power cannot be further incremented), the power will be remotely incremented under the control of the surgeon or other operator. It will be appreciated the value (in, e.g., watts) of the increments can be chosen as desired.

If the output of the "cut switch" decision diamond 94 is "no," meaning that the activated switch must have been a coag switch, a "power down" tone is generated as indicated by operational block 104 and a determination is then made whether the power setting is at a minimum as indicated by "minimum power?" decision diamond 106. If the answer is "yes," a "minimum power" tone is generated as indicated by operational block 108 while if the answer is "no," the existing power setting is decremented by one as indicated by operational block 110. Thus, if the existing power setting is not at a minimum, the power setting will be decremented under the control of the surgeon.

A delay control, indicated by "increment/decrement delay" operational block 112, is provided so as to enable the power to be incremented or decremented at a constant, faster or slower speed.

Referring again to FIG. 4, as mentioned previously, if a successful double activation sequence is completed as described above, an acceptance tone is turned on (block 76) and the remote power adjust mode is canceled (decision diamond 78 and block 82).

It will be understood that modern electrosurgical generators corresponding to generator 10 of FIG. 1 include a central processing unit (CPU) and this CPU can be programmed to carry out the program sequence or steps described above in connection with FIGS. 4 and 5. Inputs would be provided from the switches 22, 24 and 26, 28 so that computer can monitor whether the individual switches are on or off as well as what kind of switch, cut or coag, is on (see decision diamond 94). It will also be understood that a conventional generator further includes power controls, and that the power settings can be set electrically, in addition to manually, i.e., by using the generator control knobs. In order to explore these points further, reference is made to FIG. 6, which is a block diagram of a typical electrosurgical generator or unit (ESU) corresponding to the generator or ESU 10 of FIG. 1.

Figure 6:
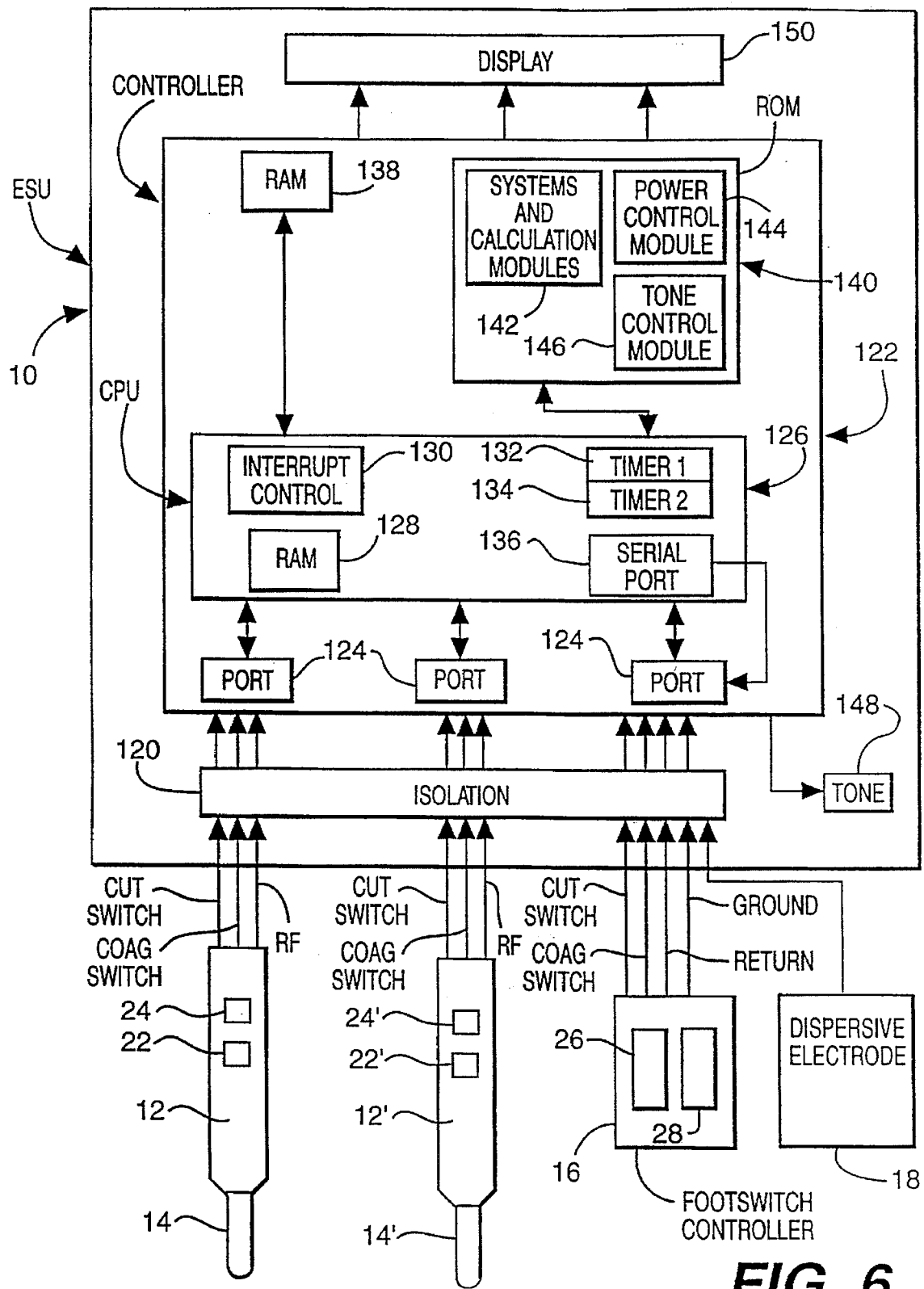
FIG. 6 is a schematic block diagram of a representative electrosurgical generator system of the type in which the invention can be incorporated.

In FIG. 6, ESU 10 is shown as connected to a first handpiece 12 corresponding to that shown in FIG. 1, a second similar handpiece 12' (including an electrode 14', a cut switch 22' and a coag switch 24'), a foot switch controller 16 corresponding to that shown in FIG. 1, and a dispersive electrode (return pad) 18, also corresponding to that shown in FIG. 1. It will be understood that a conventional ESU will typically include an input for a second handpiece and handpiece 12' simply represents such a second handpiece.

As illustrated, the handpieces 12 and 12' each have three input lines corresponding to those shown in FIG. 2, viz., a cut switch line, a coag switch line, and an RF line, (although it will be understood other connections may be provided as desired), and a plug (not shown) corresponding to plug 20 of FIG. 2 is used to connect each of the handpieces to the ESU 10. Similarly, footswitch 16 includes cut switch, coag switch, return and ground lines corresponding to those shown in FIG. 3 and is plugged into ESU by a plug (not shown) corresponding to plug 30 of FIG. 3.

As illustrated, ESU 10 includes an isolation circuit or buffer 120 which provides isolation between the inputs to ESU 10 and a controller 122. Controller 122 includes a plurality of input/output (IO) ports 124 for a conventional central processing unit (CPU) 126. CPU 126 includes a random access memory (RAM) 128, an interrupt control 130, a plurality of timers, represented by timers 132 (timer 1) and 134 (timer 2), and a serial port 136. It will be appreciated that the timers 132 and 134 perform the timing (delay) functions described above in connection with FIGS. 4 and 5.

The controller 122 also includes a further RAM 138 as well as a read only memory (ROM) 140. ROM 140 includes a plurality of modules used in controlling the operation of ESU 10 including systems and calculation modules 142, a power control module 144 and a tone control module 146.

As shown, the controller 122 also includes one or more tone generators, indicated by tone generator 148 and an output display 150.

It will be understood that power control module 144 of ROM 140 controls the power settings of the ESU 10 and, under the control of CPU 126, would provide the adjustment of the power settings described above in connection with FIGS. 4 and 5. Similarly, tone control module 146, as controlled by CPU 126, controls the generation, by tone generator 148, of the various tones described above in connection with FIGS. 4 and 5.

Those skilled in the art will appreciate that the showing of ESU 10 in FIG. 6 is intended to illustrate schematically the basic elements of a representative electrosurgical generator including those elements which cooperate to carry out the functions and operations previously described. Although the ESU shown is meant to be representative, other electrosurgical generators of a different layout, configuration or make-up can, of course, also be employed to carry out these functions and operations.

Although the present invention has been described relative to specific exemplary embodiments thereof, it will be understood by those skilled in the art that variations and modifications can be effected in these exemplary embodiments without departing from the scope and spirit of the invention.

WHAT IS CLAIMED IS:

1. An electrosurgical generator system, said system comprising:

an electrosurgical generator for producing electrosurgical power, an electrosurgical handpiece including an active electrode for receiving said electrosurgical power from said generator, a first coagulation mode switch connected to said electrosurgical generator for, when in an activated state, providing a coagulation mode of operation of said generator, and a first cut mode switch connected to said electrosurgical generator for, when in an activated state, providing a cut mode of operation of said generator, and a foot activated switch device including a second coagulation mode switch connected to said electrosurgical generator for, when in an activated state, providing said coagulation mode of operation of said generator and a second cut mode switch connected to said electrosurgical generator for, when in an activated state, providing said cut mode of operation of said generator, said generator including signal processing means connected to said handpiece and said foot activated switch device for monitoring for the activated state of at least one switch of said first and second coagulation mode switches and said first and second cut mode switches so as to detect any activation of the at least one switch being monitored, and for, responsive to at least two successive activations of only a single switch of the at least one switch being monitored, providing control of the power produced by said electrosurgical generator by further activation of said single switch.

2. A system as claimed in claim 1, wherein said signal processing means monitors the activated state of all of said switches.

3. A system as claimed in claim 2, wherein said electrosurgical generator includes a plurality of incremental power settings ranging between a maximum setting and a minimum setting, and said signal processing means determines whether said single switch is a coagulation mode switch or a cut mode switch and provides for, responsive to said single switch being a cut mode switch, incrementing an existing power setting if that setting is less than said maximum setting and for, responsive to said single switch being a coagulation mode switch, decrementing the existing power setting if that setting is greater than said minimum setting.

4. A system as claimed in claim 2, further comprising tone generator means, controlled by said signal processing means, for generating a first tone when said single switch is a cut mode switch and for generating a second tone when said single switch is a coagulation mode switch.

5. A system as claimed in claim 2 wherein said signal processing means executes a test sequence prior to providing control of the power produced by said generator wherein activation of said coagulation mode switches and cut mode switches are monitored, said signal processing means canceling said test sequence when activation of a said switch does not meet a predetermined requirement.

6. A system as claimed in claim 5, wherein said signal processing means includes timing means controlled so as to measure time periods during which said switches are activated, said signal processing means canceling said test sequence when a measured time period during a said switch is activated falls outside of a predetermined time limit.

7. A system as claimed in claim 5, wherein said signal processing means includes timing means controlled so as to measure time periods between which said switches are activated, said signal processing means canceling said test sequence when a measured time period between activations of a said switch falls outside of a predetermined time limit.

8. A system as claimed in claim 5, wherein said signal processing means includes timing means controlled so as to measure time periods during which and between which said switches are activated, said signal processing means canceling said test sequence when a measured time period during a said switch is activated falls outside of a predetermined time limit or when a measured time period between activations of a said switch falls outside of a predetermined time limit.

9. An electrosurgical generator system, said system comprising:

an electrosurgical generator for producing electrosurgical power, an electrosurgical handpiece including an active electrode for receiving said electrosurgical power from said generator, a first coagulation mode switch connected to said electrosurgical generator for, when activated, providing a coagulation mode of operation of said generator, and a first cut mode switch connected to said electrosurgical generator for, when activated, providing a cut mode of operation of said generator, and a foot activated switch device including a second coagulation mode switch connected to said electrosurgical generator for, when activated, providing said coagulation mode of operation of said generator and a second cut mode switch connected to said electrosurgical generator for, when activated, providing said cut mode of operation of said generator, said generator including signal processing means connected to said handpiece and said foot activated switch device for monitoring said first and second coagulation mode switches and said first and second cut mode switches so as to detect any activation of said switches, and for, responsive to at least two successive activations of only a single switch of said switches, providing a power adjustment mode wherein the power produced by said electrosurgical generator can be controlled by further activation of said single switch.

10. A system as claimed in claim 9, wherein said electrosurgical generator includes a plurality of incremental power settings ranging between a maximum setting and a minimum setting, and said signal processing means determines whether said single switch is a coagulation mode switch or a cut mode switch and provides for, responsive to said single switch being a cut mode switch, incrementing an existing power setting existing when said power adjustment mode is provided if that setting is less than said maximum setting and for, responsive to said single switch being a coagulation mode switch, decrementing the existing power setting if that setting is greater than said minimum setting.

11. A system as claimed in claim 9, further comprising tone generator means, controlled by said signal processing means, for generating a first tone when said power adjustment mode is entered, for generating a second tone during said power adjustment mode when said single switch is a cut mode switch and for generating a third tone during said power adjustment mode when said single switch is a coagulation mode switch.

12. A system as claimed in claim 9 wherein said signal processing means executes a power adjustment mode test sequence prior to entering said power adjustment mode wherein activation of said coagulation mode switches and cut mode switches are monitored, said signal processing means canceling said test sequence when activation of a said switch does not meet a predetermined requirement.

13. A system as claimed in claim 12, wherein said signal processing means includes timing means controlled so as to measure time periods during which said switches are activated, said signal processing means canceling said power adjustment mode test sequence when a measured time period during a said switch is activated falls outside of a predetermined time limit.

14. A system as claimed in claim 12, wherein said signal processing means includes timing means controlled so as to measure time periods between which said switches are activated, said signal processing means canceling said power adjustment mode test sequence when a measured time period between activations of a said switch falls outside of a predetermined time limit.

15. A system as claimed in claim 12, wherein said signal processing means includes timing means controlled so as to measure time periods during which, and between which, said switches are activated, said signal processing means canceling said power adjustment mode test sequence when a measure time period during which a said switch is activated falls outside of a predetermined time limit or when a measured time period between activations of a said switch falls outside of a predetermined time limit.

16. An electrosurgical generator system, said system comprising:

an electrosurgical generator for producing electrosurgical power, an electrosurgical handpiece including an active electrode for receiving said electrosurgical power from said generator, a first coagulation mode switch connected to said electrosurgical generator for, when activated, providing a coagulation mode of operation of said generator, and a first cut mode switch connected to said electrosurgical generator for, when activated, providing a cut mode of operation of said generator, and a foot activated switch device including a second coagulation mode switch connected to said electrosurgical generator for, when activated, providing said coagulation mode of operation of said generator and a second cut mode switch connected to said electrosurgical generator for, when activated providing said cut mode of operation of said generator, said generator including signal processing means connected to said handpiece and said foot activated switch device for monitoring said first and second coagulation mode switches and said first and second cut mode switches so as to detect any activation of said switches, and for, responsive to at least two successive activations of only a single switch of said switches, providing entry from a normal mode into a power adjustment mode wherein the power produced by said electrosurgical generator can be controlled by further activation of said single switch, and for providing return to said normal mode from said power adjustment mode responsive to at least two further successive activations of said single switch.

17. A system as claimed in claim 16, wherein said electrosurgical generator includes a plurality of incremental power settings ranging between a maximum setting and a minimum setting, and said signal processing means determines whether said single switch is a coagulation mode switch or a cut mode switch and provides for, responsive to said single switch being a cut mode switch, incrementing an existing power setting existing when said power adjustment mode is provided if said setting is less than said maximum setting and for, responsive to said single switch being a coagulation mode switch, decrementing the existing power setting if that setting is greater than said minimum setting.

18. A system as claimed in claim 16, further comprising tone generator means, controlled by said signal processing means, for generating a first tone when said power adjustment is entered, for generating a second tone during said power adjustment mode when said single switch is a cut mode switch and for generating a third tone during said power adjustment mode when said single switch is a coagulation mode switch.

19. A system as claimed in claim 16 wherein said signal processing means executes a power adjustment mode test sequence prior to entering said power adjustment mode wherein activation of said coagulation mode switches and cut mode switches are monitored, said signal processing means canceling said test sequence when activation of a said switch does not meet a predetermined requirement.

20. A system as claimed in claim 18, wherein said signal processing means includes timing means controlled so as to measure time periods during which said switches are activated, said signal processing means canceling said power adjustment mode test sequence when a measured time during a said switch is activated falls outside of a predetermined time limit.

21. A system as claimed in claim 18, wherein said signal processing means includes timing means controlled so as to measure time periods between which said switches are activated, said signal processing means canceling said power adjustment mode test sequence when a measured time period between activations of a said switch falls outside of a predetermined time limit.

22. A system as claimed in claim 18, wherein said signal processing means includes timing means controlled so as to measure time periods during which and between which said switches are activated, said signal processing means canceling said power adjustment mode test sequence when a measured time period during which a switch is activated falls outside of a predetermined time limit or when a measured time between activations of a said switch falls outside of a predetermined time limit.

* * * * *